(12) United States Patent
Vallera et al.

(10) Patent No.: US 6,846,484 B2
(45) Date of Patent: Jan. 25, 2005

(54) DTAT FUSION TOXIN

(75) Inventors: Daniel A. Vallera, St. Louis Park, MN (US); Walter A. Hall, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 10/033,577

(22) Filed: Dec. 28, 2001

(65) Prior Publication Data

US 2003/0124147 A1 Jul. 3, 2003

(51) Int. Cl.[7] .................. A61K 38/49; A61K 39/05; A61K 38/00; A61K 35/14
(52) U.S. Cl. ............... 424/94.63; 424/238.1; 514/12; 514/802; 530/380
(58) Field of Search .................. 514/12, 802; 530/380; 424/94.63, 238.1

(56) References Cited

U.S. PATENT DOCUMENTS

| | | | |
|---|---|---|---|
| 4,340,535 A | | 7/1982 | Voisin et al. |
| 4,545,985 A | | 10/1985 | Pastan et al. |
| 4,675,382 A | | 6/1987 | Murphy |
| 4,831,112 A | | 5/1989 | Kobayashi et al. |
| 5,208,021 A | | 5/1993 | Johnson et al. |
| 5,591,631 A | * | 1/1997 | Leppla et al. |
| 5,709,843 A | | 1/1998 | Reisner |
| 5,720,720 A | | 2/1998 | Laske et al. |
| 5,728,383 A | | 3/1998 | Johnson et al. |
| 5,792,458 A | | 8/1998 | Johnson et al. |
| 5,894,018 A | | 4/1999 | Davila et al. |
| 6,001,329 A | | 12/1999 | Buchsbaum et al. |

FOREIGN PATENT DOCUMENTS

| | | | |
|---|---|---|---|
| WO | WO 94/26308 | * | 11/1994 |
| WO | WO 96/13599 | * | 5/1996 |
| WO | WO 00/04926 | * | 2/2000 |

OTHER PUBLICATIONS

Morishita et al (Nucleic Acids symposium series, 1996, vol. 35, pp. 291–292).*
Baty et al (Molecular Microbiology, 1988, vol. 2, pp. 807–811).*
Olsnes et al (Journal of Biological Chemistry, 1982, vol. 257, pp. 13263–13270).*
Greenfield et al (Science, 1987, vol. 238, pp. 536–539).*
el Kouhen et al (European Journal of Biochemistry, 1993, vol. 214, pp. 635–639).*
Geoff et al (Protein engineering, 1997, vol. 10, suppl. p. 5).*
Bouveret et al (Molecular Microbiology, 1997, vol. 23, pp. 909–920).*
Lacy et al (Journal of Molecular Biology, 1999, vol. 291, pp. 1091–1104).*
Wiedlocha et al (Cancer research, 1991, vol. 51, pp. 916–920).*
GenBank Accession No. E01560.
GenBank Accession No. K01722.
Collier and Kandel, "Structure and Activity of Diphtheria Toxin," *J. Biol. Chem.*, 1971, 246(5):1496–1503.
Collier, "Structure and Activity of Diphtheria Toxin," *ADP–Ribosylation Reactions—Biology and Medicine*, 1982, Academic Press, New York, Chapter 34, pp. 575–592.
Davis et al., "Survival rates in patients with primary malignant brain tumors stratified by patient age and tumor histological type: an analysis based on Surveillance, Epidemiology, and End Results (SEER) data, 1973–1991," *J. Neurosurg.*, 1998, 88:1–10.
Fabbrini et al., "The amino–terminal fragment of human urokinase directs a recombinant chimeric toxin to target cells: internalization is toxin mediated," *Faseb J.*, 1997, 11:1169–1176.
Greenfield et al., "Nucleotide sequence of the structural gene for diphtheria toxin carried by corynebacteriophage β," *Proc. Natl. Acad. Sci. USA*, 1983, 80:6853–6857.
Kreitman, "Immunotoxins in cancer therapy," *Curr. Opin. Immunol.*, 1999, 11:570–578.
Laske et al., "Tumor regression with regional distribution of the targeted toxin TF–CRM107 in patients with malignant brain tumors," *Nature Medicine*, 1997, 3(12):1362–1368.
Marshall, "A New Phase in the War on Cancer," *Science*, 1995, 267:1412–1415.
McKeever, "Insights About Brain Tumors Gained Through Immunohistochemistry and in Situ Hybridization of Nuclear and Phenotypic Markers," *J. Histochem. Cytochem.*, 1998, 45(5):585–594.
Mori et al., "Up–regulation of urokinase–type plasminogen activator and its receptor correlates with enhanced invasion activity of human glioma cells mediated by transforming growth factor–α or basic fibroblast growth factor," *J. Neuro–Oncology*, 2000, 46:115–123.
Moskaug et al., "Translocation of Diphtheria Toxin A–fragment to the Cytosol," *J. Biol. Chem.*, 1989, 264(26):15709–15713.
Oldfield and Youle, "Immunotoxins for Brain Tumor Therapy," *Current Topics in Microbiology and Immunology*, 1998, 234:97–114.
Pastan and FitzGerald, "Pseudomonas Exotoxin: Chimeric Toxins," *J. Biol. Chem.*, 1989, 264(26):15157–15160.
Rajagopal and Kreitman, "Recombinant Toxins That Bind to the Urokinanse Receptor Are Cytotoxic without Requiring Binding to the $\alpha_2$–Macroglobulin Receptor," *J. Biol. Chem.*, 2000, 275(11):7566–7573.

(List continued on next page.)

*Primary Examiner*—Karen A. Canella
(74) *Attorney, Agent, or Firm*—Fish & Richardson P.C., P.A.

(57) ABSTRACT

The invention provides fusion toxins that contain one or more regions of diphtheria toxin and a portion of urokinase-type plasminogen activator, as well as the nucleic acids that encode the fusion toxins and methods of using the fusion toxins.

24 Claims, 10 Drawing Sheets

OTHER PUBLICATIONS

Figure 1:
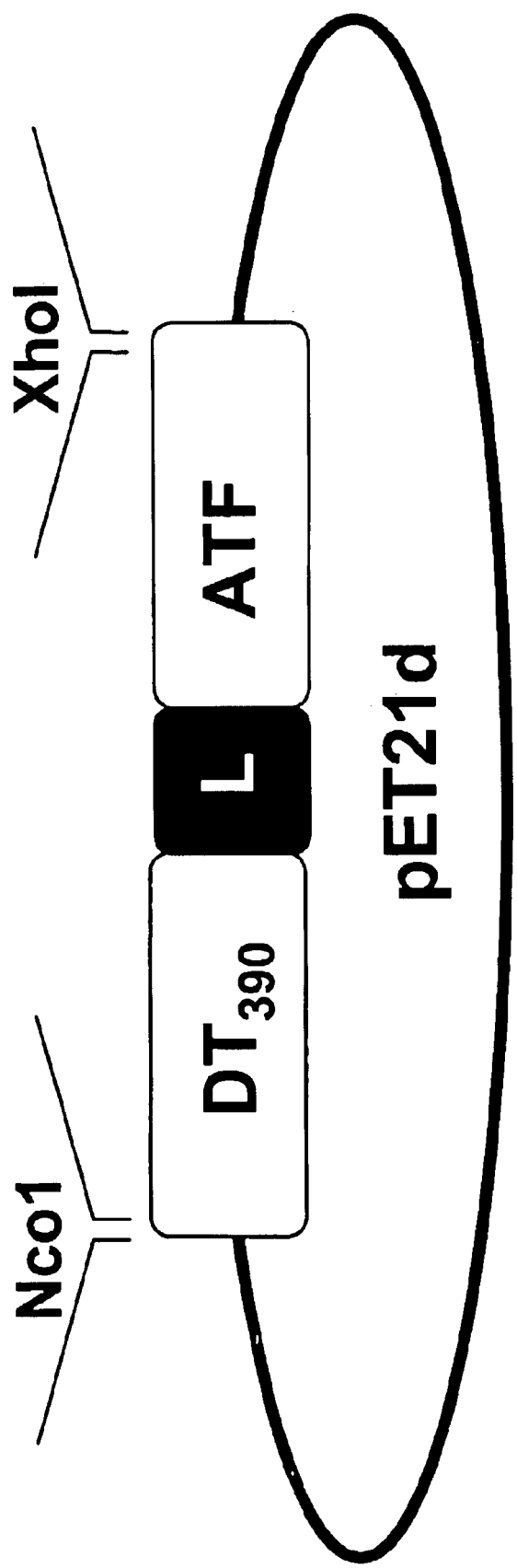

Ramakrishnan et al., "Vascular Endothelial Growth Factor–Toxin Conjugate Specifically Inhibits KDR/flk–1–positive Endothelial Cell Proliferation in Vitro and Angiogenesis in Vivo," *Cancer Res.*, 1996, 56:1324–1330.

Vallera et al., "Anti–Graft–Versus–Host Disease Effect of $DT_{390}$–Anti–CD3sFv, a Single–Chain Fv Fusion Immunotoxin Specifically Targeting the CD3ε Moiety of the T–Cell Receptor," *Blood*, 1996, 88(6):2342–2353.

Vallera et al., "Renal Dysfunction accounts for the dose limiting toxicity of $DT_{390}$anti–CD3sFv, a potential new recombinant anti–GVHD immunotoxin," *Protein Engin.*, 1997, 10(9):1071–1076.

Vallera et al., "Retroviral Immunotoxin Gene Therapy of Acute Myelogenous Leukemia in Mice Using Cytotoxic T Cells Transduced with an Interleukin 4/Diphtheria Toxin Gene," *Cancer Res.*, 2000, 60:976–984.

* cited by examiner

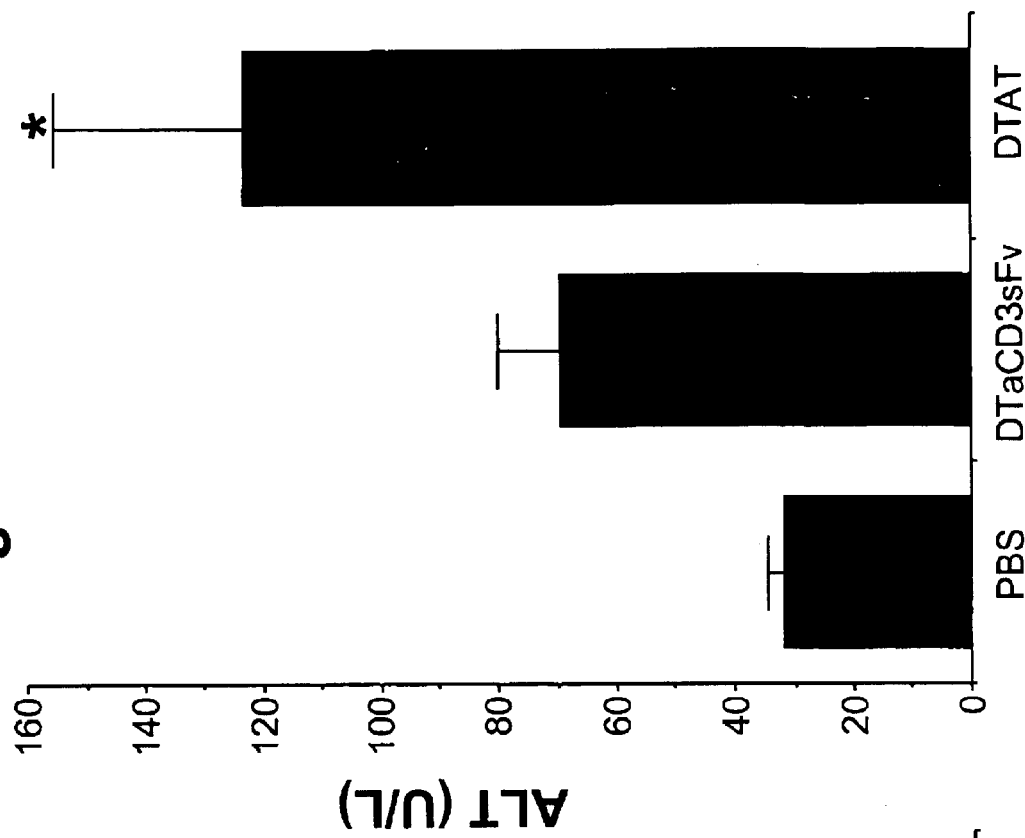
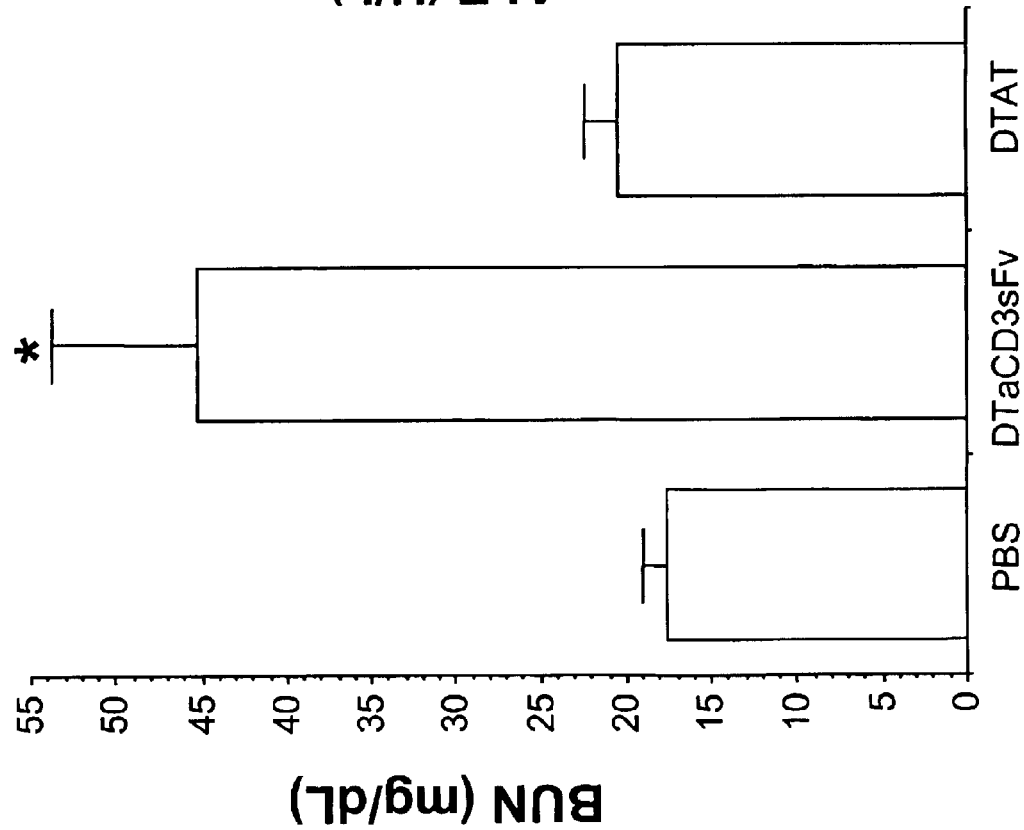

DTAT FUSION TOXIN

TECHNICAL FIELD

This invention relates to fusion toxins that are useful for targeting pathogenic cells. More particularly, this invention relates to fusion toxins that are polypeptides containing a toxin domain, an internalization domain, and a targeting domain that is a fragment of the urokinase-type plasminogen activator.

BACKGROUND

Toxin proteins such as diphtheria toxin (DT) typically are made up of several functional domains, which may include a toxin (i.e., killing) domain, an internalization domain (e.g., the DT translocation enhancing region (TER)), and a targeting domain to control recognition of and binding to target cells. DT is a single chain of 535 amino acids (Greenfield et al. (1983) *Proc. Natl. Acad. Sci. USA* 80:6853–6857), which upon mild trypsinization and reduction in vitro breaks into an A chain and a B chain (Collier et al. (1971) *J. Biol. Chem.* 246:1496–503; and Moskaug et al. (1989) *J. Biol. Chem.* 264:15709–15713). The B chain contains the targeting domain and the TER, which facilitates translocation of the A chain into the cytoplasm. Once in the cytoplasm, the toxin domain within the A chain catalyzes ADP-ribosylation of a translationally modified histidine residue (diphthamide) on elongation factor-2, leading to the arrest of protein synthesis and subsequent cell death (Collier et al., *ADP Ribosylation Reactions: Biology and Medicine*, Academic Press, Inc., New York, p. 573 (1982)). Other toxins (e.g., ricin) have similar A and B chain structures, while toxins such as the Pseudomonas exotoxin have similar domains but in a single chain structure.

Fusion toxins can be therapeutically useful in pathological conditions such as cancer, and particularly in types of cancer (e.g., certain brain cancers) that are unresponsive to treatment by chemotherapy and radiation. Fusion toxins are chimeric polypeptides that typically contain a toxin protein or a toxin domain from a toxin protein, and a targeting domain from a heterologous protein (Kreitman (1999) *Curr. Opin. Immunol.* 11:570–578; and Oldfield and Youle (1998) *Curr. Top. Microbiol. Immunol.* 234:97–114). Fusion toxins may incorporate a portion of a toxin protein or an entire toxin protein (see, for example, Pastan and FitzGerald (1989) *J. Biol. Chem.* 264:15157–15160). Fusion toxins that contain an entire toxin molecule, however, typically result in non-specific killing mediated by binding to non-target cells. Fusion toxins that contain only the toxin (killing) domain of a toxin protein, while much more specific, are much less toxic because they lack the translocation enhancing region that facilitates entry of the toxin domain into target cells.

Malignancies of the central nervous system are the third leading cause of cancer-related deaths among adolescents and adults from 15 to 34 years of age (Davis et al. (1998) *J. Neurosurg.* 88:1–10). Patients with such malignancies typically have a two-year survival rate of less than 20% (Thompson (1995) *Science* 267:1414). Although the anatomy of brain tumors would especially lend them to intratumoral therapy with agents such as fusion toxins, therapeutic approaches to treating such tumors are complicated by the fact that there has been no known tumor-specific marker that can be targeted in the majority of patients (McKeever (1998) *J. Histochem. Cytochem.* 46:585–594).

SUMMARY

The present invention is based on the discovery that urokinase-type plasminogen activator receptors (uPAR) are selectively overexpressed in glioblastoma multiforme, an aggressive form of brain cancer (Mori et al. (2000) *J. Neurooncol.* 46:115–123). In addition, uPAR expression is correlated with the invasive activity of glioma cells. uPAR also is overexpressed in a number of other tumors, including cancers of the breast, skin, colon, ovaries, thyroid, stomach, liver, and prostate (see Fabbrini et al. (1997) *FASEB J.* 11:1169–1176; and Rajagopal and Kreitman (2000) *J. Biol. Chem.* 275:7566–7573). Furthermore, uPAR is expressed on the endothelial cells that make up tumor microvasculature.

The discovery that glioblastoma tumors overexpress uPAR allows for targeting glioblastoma tumor cells with fusion toxins containing uPA, the ligand for these receptors. As described above, such fusion toxins will be most useful if they incorporate the killing and translocation domains of a toxin such as DT, while omitting the targeting domain of the toxin protein.

In one aspect, the invention provides a method for killing a tumor cell. The method includes contacting a tumor cell with a fusion toxin containing the toxin domain of diphtheria toxin and a urokinase-type plasminogen activator domain. The tumor cell can be a brain tumor cell (e.g., a glioblastoma, meningioma, astrocytoma, medulloblastoma, ependymoma, or oligodendroglioma cell). The tumor cell can express the urokinase-type plasminogen activator receptor (e.g., on its surface). The contacting of the tumor cell by the fusion toxin can occur in vivo.

The fusion toxin used to kill the tumor cell can contain the translocation enhancer region of diphtheria toxin. In another embodiment, the fusion toxin can contain the amino terminal 390 amino acids of diphtheria toxin. The urokinase-type plasminogen activator domain of the fusion toxin is capable of binding to urokinase-type plasminogen activator receptor. The urokinase-type plasminogen activator domain also can contain the amino terminal fragment of urokinase-type plasminogen activator. In yet another embodiment, the fusion toxin can contain the toxin domain of diphtheria toxin, the translocation enhancing region of diphtheria toxin, and the amino-terminal fragment of urokinase-type plasminogen activator.

In another aspect, the invention provides a method for killing a glioblastoma tumor cell. The method includes contacting a glioblastoma tumor cell with a fusion toxin containing a urokinase-type plasminogen activator domain. The fusion toxin can contain a toxin domain of a toxin selected from the group consisting of diphtheria toxin, ricin, Pseudomonas exotoxin, colicin, anthrax toxin, tetanus toxin, botulinum neurotoxin, saporin, abrin, bryodin, pokeweed anti-viral protein, viscumin, and gelonin. In another embodiment, the fusion toxin also can contain an internalization domain of a toxin selected from the group consisting of diphtheria toxin, colicin, delta-Endotoxin, anthrax toxin, tetanus toxin, botulinum toxin, and Pseudomonas exotoxin.

The urokinase-type plasminogen activator domain within the fusion toxin is capable of binding to urokinase-type plasminogen activator receptor. The urokinase-type plasminogen activator domain can contain the amino-terminal fragment of urokinase-type plasminogen activator. The glioblastoma tumor cell that is contacted by the fusion toxin can express the urokinase-type plasminogen activator receptor (e.g., on its surface). The fusion toxin can contain the toxin domain of diphtheria toxin, the translocation enhancing region of diphtheria toxin, and the amino-terminal fragment of the urokinase-type plasminogen activator.

In another aspect, the invention provides a fusion toxin containing the toxin domain of diphtheria toxin and a urokinase-type plasminogen activator domain. The fusion toxin further can include the translocation enhancing region of diphtheria toxin. The urokinase-type plasminogen activator domain of the fusion toxin can contain the amino-terminal fragment of urokinase-type plasminogen activator. In another embodiment, the fusion toxin can include the toxin domain of diphtheria toxin, the translocation enhancing region of diphtheria toxin, and the amino-terminal fragment of urokinase-type plasminogen activator.

In another aspect, the invention provides a pharmaceutical composition that contains the fusion toxin of the invention. The invention also provides an article of manufacture that incorporates the pharmaceutical composition of the invention.

In yet another aspect, the invention provides a nucleic acid containing a sequence that encodes the fusion toxin of the invention, as well as vectors containing the nucleic acid. The invention also provides host cells containing such vectors and expressing a fusion toxin that can contain the toxin domain of diphtheria toxin and a urokinase-type plasminogen activator domain.

Unless otherwise defined, all technical and scientific terms used herein have the same meaning as commonly understood by one of ordinary skill in the art to which this invention belongs. Although methods and material similar or equivalent to those described herein can be used in the practice or testing of the present invention, suitable materials and methods are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a drawing of the pDTAT.pET21d expression plasmid.

FIGS. 2A and 2B are bar graphs showing the effect of DTAT on the viability of U118 MG glioblastoma cells after 48 hours of treatment (FIG. 2A) and 72 hours of treatment (FIG. 2B), versus treatment with a DThIL13 control.

FIG. 3 is a line graph depicting the effect of DTAT on the viability of U87 MG glioblastoma cells, Neuro-2a neuroblastoma cells, SKBR3 adenocarcinoma cells, and Daudi lymphoma cells.

FIG. 4 is a line graph showing the effect of DTAT on the viability of U118 MG cells, versus treatment with a DTmIL4 control.

FIG. 5 is a line graph showing the response of U118 MG glioblastoma cells to increasing doses of DTAT over 24, 48, and 72 hours of treatment.

FIG. 6 is a line graph depicting the response of HUVEC to treatment with DTAT, as compared to DTmIL4, DThIL2, DTmIL13, and DThIL13 controls.

FIG. 7 is a bar graph showing the effect of anti-DTAT antibodies on the ability of DTAT to kill HUVEC.

FIG. 8 is a line graph depicting tumor volumes in individual mice, before and after administration of DTAT.

FIG. 9 is a line graph depicting the average tumor size for groups of mice treated with DTAT, PBS, DThIL2, or DThIL13.

FIGS. 10A and 10B are bar graphs showing serum levels of Blood Urea Nitrogen (FIG. 10A) and alanine transferase (FIG. 10B) in mice injected with DTAT, PBS, or DTantiCD3sFv.

DETAILED DESCRIPTION

The present invention features fusion toxins that include at least one toxin domain and at least one ligand for a cell surface receptor. The fusion toxins may contain (a) a toxin domain (e.g., a portion of DT), (b) an internalization domain (e.g., the DT TER), and (c) a targeting domain derived from the urokinase-type plasminogen activator (uPA). uPA is a ligand for the urokinase-type plasminogen activator receptor (uPAR) that is expressed, typically overexpressed, on the surfaces of certain tumor cells. As used herein, "overexpressed" means expressed at higher levels than normally would be observed. For example, the levels of uPAR expressed on glioblastoma cells typically are higher than the levels of uPAR expressed on corresponding non-tumorigenic brain cells. In another example, the amount of DTAT produced by a cell transformed with a DTAT expression vector typically is greater than the amount produced by an untransformed cell.

In one embodiment, fusion toxins according to the present invention may contain the DT toxin domain, the DT internalization domain (TER), and the amino-terminal fragment (ATF) of uPA. This embodiment of the invention, termed DTAT, is particularly useful. Fusion toxins of the present invention can specifically inhibit the proliferation of glioblastoma cell lines in vitro; the fusion toxins also can inhibit the growth of endothelial cells in vitro. Additionally, fusion toxins of the invention can cause regression of human glioblastoma tumors in nude mice. Furthermore, the fusion toxins do not severely affect renal or hepatic function. uPAR therefore can serve as a valid target for therapy against glioblastoma tumors that are resistant to chemotherapy and radiation, and against the endothelial vasculature that feeds such tumors.

Fusion Toxins

As used herein, "polypeptide" refers to an amino acid chain, regardless of length or post-translational modification. A "functional fragment" of a polypeptide refers to a fragment of the polypeptide that is shorter than the full-length, wild-type polypeptide, but which has at least 10% (e.g., 10%, 25%, 50%, 70%, 85%, 100%, or more) of the activity of the full-length, wild-type polypeptide.

The fusion toxins of the present invention are polypeptides that contain the toxin domain of a toxin protein and a heterologous targeting domain derived from uPA. An internalization domain may also be included. As used herein, "toxin domain" refers to a polypeptide or functional fragment thereof that mediates a cytotoxic effect on a cell. Suitable toxin domains can be, by way of example and not limitation, the toxin domains of DT, ricin, Pseudomonas exotoxin, colicin, anthrax toxin, tetanus toxin, botulinum neurotoxin, saporin, abrin, bryodin, pokeweed anti-viral protein, viscumin, and gelonin. The DT toxin domain is particularly useful. Functional fragments of the DT A chain that contain the toxic function of DT also are particularly useful. Furthermore, fusion toxins of the invention may include more than one (e.g., 2, 3, 4, or more) toxin domains or functional fragments thereof. When multiple toxin domains are included, they may be immediately adjacent to each other, separated by one or more targeting domains or internalization domains, or separated by a linker or linkers.

The amino acid sequence of a toxin domain of the invention can be identical to the wild-type sequence of the naturally occurring toxin domain (e.g., the DT toxin domain). Alternatively, a toxin domain can contain amino acid deletions, additions, or substitutions, provided that the toxin domain has at least 10% (e.g., 10%, 25%, 50%, 70%, 85%, 100%, or more) of the ability of the wild-type polypeptide to kill relevant target cells. In vitro and in vivo methods for comparing the relative activities of two or more toxins, whether naturally occurring toxins or fusion toxins, are known to those skilled in the art. Amino acid substitutions typically will be conservative substitutions, although non-conservative substitutions (e.g., deletions and insertions) also are possible. Conservative substitutions generally have little effect on the hydrophobicity of the polypeptide or the bulk of residue side chains, and typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The fusion toxins of the present invention may contain an internalization domain. As used herein, "internalization domain" refers to a polypeptide or functional fragment thereof that confers the ability to translocate through the cell surface, across the cellular membrane and into the cytoplasm. An internalization domain typically is critical for the function of a fusion toxin, since a toxin cannot kill a cell unless it is internalized. Suitable internalization domains include any polypeptide that mediates transfer of a protein through the cellular membrane.

The internalization domain of DT (i.e., the TER), which is part of the DT B chain, is particularly useful for the fusion toxins of the invention. Alternatively, fusion toxins may include internalization domains from other bacterial toxins that are adept at opening channels in the lipid bilayer of the cellular membrane in order to facilitate translocation. These include, by way of example and not limitation, colicin, delta-Endotoxin, anthrax toxin, tetanus toxin, botulinum neurotoxin, and Pseudomonas exotoxin. Fusion toxins therefore can incorporate the internalization domain of any such molecule.

In one embodiment, the fusion toxins of the invention include both the toxin domain and the internalization domain of DT. For example, as with DTAT, a fusion toxin may contain the N-terminal 390 amino acids of DT, which contain the toxin domain and the TER. Alternatively, a fusion toxin may contain only those regions within the N-terminal 390 amino acids that actually confer the killing and internalization functions.

Fusion toxins of the invention also include a targeting domain that contains uPA or a portion of uPA. As used herein, "targeting domain" refers to a polypeptide or functional fragment thereof that has significant binding affinity for a target molecule on the surface of a target cell. In immunotoxins, for example, the target molecule is a cell surface antigen and the targeting domain is an antibody. For fusion toxins such as DTAT, the target is a cell surface receptor and the targeting domain is a ligand for the receptor. According to the present invention, the targeting domain contains uPA or any portion of uPA capable of binding to uPAR on the surfaces of target cells. The ATF of uPA is particularly useful. The ATF includes the receptor-binding domain of uPA but does not include the catalytic or internalization domains.

Fusion toxin targeting domains of the invention may include the entire ATF (i.e., the amino-terminal 135 amino acids of uPA.) These residues include the receptor-binding domain, which is an epidermal growth factor-like domain situated between amino acids 12 and 32, and which binds to uPAR with high affinity ($K_d$=0.5 nM). Alternatively, fusion toxins may contain a targeting domain that is a functional fragment of the uPA ATF.

Fusion toxin targeting domains of the present invention can have amino acid sequences that are identical to the wild-type sequence of the uPA ATF. Alternatively, a targeting domain may contain amino acid deletions, additions, or substitutions, provided that the targeting domain has at least 10% (e.g., 10%, 25%, 50%, 70%, 85%, 100%, or more) of the ability of the wild-type uPA polypeptide to bind to the target molecule. Methods of comparing the relative ability of two of more molecules (e.g., fusion toxins or ligands) to bind to a target cell are well known in the art. Amino acid substitutions typically will be conservative substitutions (see above), although non-conservative substitutions are possible.

The toxin domains, internalization domains, and targeting domains within the fusion toxins of the invention can be positioned in any orientation with respect to each other. For example, a toxin domain can be N-terminal of an internalization domain and a targeting domain, or a targeting domain or an internalization domain can be at the N-terminus. The three domains can be immediately adjacent to each other and coupled via peptide bonds, or they can be coupled via a linker or linkers. In one embodiment, such linkers can be peptides (in which case the coupling is again via peptide bonds, as in DTAT). Alternatively, cross-linking agents or hetero bifunctional cross-linking agents (e.g., cystamine, m-Maleimidobenzoyl-N-hydroxysuccinimide-ester, N-succinimidyl-3-(2-pyridyldithio)-propionate, methylmercaptobutyrimidate, or dithiobis(2-nitrobenzoic acid) can be utilized to generate disulfide or thioether bonds between the domains.

The fusion toxins of the invention also can be modified for use in vivo by the addition, at the amino- or carboxy-terminal ends, of a blocking agent to facilitate survival of the fusion toxins in vivo. This can be useful in situations in which peptide termini tend to be degraded by proteases prior to cellular uptake. Such blocking agents can include, without limitation, additional related or unrelated peptide sequences that can be attached to the amino- and/or carboxy-terminal residues of the fusion toxins to be administered. Blocking can be achieved either chemically during the synthesis of the fusion toxins or by recombinant DNA technology using methods familiar to those of ordinary skill in the art. Alternatively, blocking agents such as pyroglutamic acid or other molecules known in the art can be attached to the amino- and/or carboxy-terminal residues, or the amino group at the amino terminus or the carboxyl group at the carboxy terminus can be replaced with a different moiety.

Fusion toxins of the present invention (e.g., DTAT) can be produced by standard methods, combining in vitro recombinant DNA techniques to produce vectors comprising nucleotide sequences that encode the fusion toxins, overexpression of the fusion toxins in host cells, and biochemical purification of the resulting cellular extracts. Such expression vectors, containing relevant coding sequences and appropriate transcriptional/translational control signals, can be constructed using, for example, methods well known to those of ordinary skill in the art. See, for example, techniques described in Sambrook et al., *Molecular Cloning: A Laboratory Manual* (2nd Ed.), Cold Spring Harbor Laboratory, New York (1989); and Ausubel et al., *Current Protocols in Molecular Biology*, Green Publishing Associates and Wiley Interscience, New York (1989). See also the following subsection and Example 1, below.

Expression systems that can be used for small or large scale production of the fusion toxins of the invention include, but are not limited to, microorganisms such as bacteria (e.g., *E. Coli* and *B. subtilis*) transformed with recombinant bacteriophage DNA, plasmid DNA, or cosmid DNA expression vectors containing the nucleic acid molecules of the invention; yeast (e.g., *S. cerevisiae*) transformed with recombinant yeast expression vectors containing the nucleic acid molecules of the invention; insect cell systems infected with recombinant virus expression vectors (e.g., baculovirus) containing the nucleic acid molecules of the invention; plant cell systems infected with recombinant virus expression vectors (e.g., tobacco mosaic virus) or transformed with recombinant plasmid expression vectors (e.g., Ti plasmid) containing the nucleic acid molecules of the invention; or mammalian cell systems (e.g., COS, CHO, HeLa, 293, and 3T3 L1 cells) harboring recombinant expression constructs containing promoters derived from the genome of mammalian cells (e.g., the metallothionein promoter) or from mammalian viruses (e.g., the adenovirus late promoter or the cytomegalovirus promoter), along with the nucleic acid molecules of the invention. Also useful as host cells are primary or secondary cells obtained directly from a mammal, transfected with a plasmid vector or infected with a viral vector that contains the nucleic acids of the invention.

Nucleic Acids

The invention provides nucleic acids encoding the above polypeptides of the invention. As used herein, the term "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). Nucleic acids of the invention may have sequences identical to those of nucleic acids encoding the wild-type toxin, internalization, and targeting domains that are incorporated into the fusion toxins of the invention. Alternatively, nucleic acids of the invention may contain codons other than wild-type codons which, due to the degeneracy of the genetic code, encode toxin, internalization, or targeting domains with amino acid sequences identical to relevant wild-type polypeptides. Furthermore, the nucleic acids may encode toxin, internalization, or targeting domains that are not identical to the wild type polypeptide due to the presence of, for example, any of the above described deletions, additions, or substitutions.

Nucleic acids of the invention may be hybrid genes. As used herein, "hybrid gene" refers to a nucleic acid molecule that encodes amino acid sequences from more than one polypeptide. Hybrid genes of the invention typically will contain a first portion and a second portion, and may contain more portions (e.g., a third portion, a fourth portion, or more portions). For example, a first portion may encode the DT toxin domain, a second portion may encode an internalization domain, and a third portion may encode a targeting domain comprising the uPA ATF. These portions may be arranged in any order relative to one another, and between any of the portions can be codons encoding a linker (see above and Example 1).

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention typically are expression vectors. An "expression vector" is a vector that includes expression control sequences, and an "expression control sequence" is a DNA sequence that controls and regulates the transcription and translation of another DNA sequence.

In the expression vectors of the invention, the nucleic acid sequence encodes a fusion toxin with an initiator methionine, operably linked to one or more transcriptional regulatory elements. As used herein, "operably linked" means incorporated into a genetic construct so that expression control sequences effectively control expression of a coding sequence of interest. Examples of transcriptional regulatory elements include promoters, enhancers, and transcription terminating regions. A promoter is a transcriptional regulatory element composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of transcriptional and translational control sequences in a cell when RNA polymerase is able to transcribe the coding sequence into mRNA, which then is translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The expression vectors of the invention, which contain nucleic acid sequences encoding fusion toxins, have a variety of uses. For example, they can be used to transform or transfect either prokaryotic (e.g., bacteria) or eukaryotic (e.g., yeast, plant, insect, or mammalian) cells. Such cells then may be used for small or large scale in vitro production of fusion toxins by methods such as those known in the art (see preceding subsection, above, and Example 1, below). These methods may involve, for example, culturing the cells under conditions that maximize production of the fusion toxin, and isolating the fusion toxin from the cells or from culture medium. Transformed/transfected cells also can be used for delivery of a fusion toxin to a target cell by administration of the transformed/transfected cells to the target cells.

Methods for Using Fusion Toxins

The fusion toxins of the invention can be administered to a cell population in order to kill those cells that have surface expression of the target molecule for the targeting domain. Fusion toxins (e.g., DTAT) can be administered as therapeutic agents, for example, when it is desired to eliminate a cell population (e.g., a tumor) that expresses the uPAR target. Furthermore, fusion toxins can be administered either ex vivo or in vivo.

In one embodiment, fusion toxins of the present invention can be administered to target cells derived from tumors. Through such an ex vivo approach, the effectiveness of various preparations of the fusion toxins can be evaluated before they are used for in vivo approaches. Methods for quantifying the toxicity of one or more fusion toxins are known to those skilled in the art (e.g., as in Example 1).

In another embodiment, fusion toxins such as DTAT can be incorporated into pharmaceutical compositions and administered to a subject that exhibits tumor growth. Tumors suitable for treatment by fusion toxins such as DTAT include, by way of example and not limitation, glioblastoma, meningioma, astrocytoma, medulloblastoma, ependymoma, and oligodendroglioma. Generally, pharmaceutical compositions of the invention contain one or more fusion toxins suspended in a pharmaceutically acceptable carrier. A "pharmaceutically acceptable carrier" is a pharmaceutically acceptable solvent, suspending agent, or any other pharmacologically inert vehicle for delivering one or more therapeutic compounds (e.g., fusion toxins such as DTAT) to a subject. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Fusion toxins of the invention can be administered in any of a number of ways. For example, fusion toxins may be administered orally or by intravenous infusion, or they may be injected subcutaneously, intramuscularly, intratumorally, intraperitoneally, intrarectally, intravaginally, intranasally, intragastrically, intratracheally, or intrapulmonarily. Intratumoral injection is particularly useful, since it allows a fusion toxin to be delivered directly to the appropriate tissue (e.g., brain tissue where tumor growth is occurring). Such direct delivery can results in concentration of a fusion toxin at the affected tissue, while avoiding or greatly reducing systemic effects on non-target tissues. The dosage required will depend on the route of administration, the nature of the composition, the nature of the subject's illness, and the subject's size, weight, surface area, age, and sex, other drugs being administered, and the judgment of the attending physician. Wide variations in the necessary dosage are to be expected in view of the differing efficiencies of various routes of administration. For example, oral administration would be expected to require higher dosages than administration by injection. Variations in these dosage levels can be adjusted using standard empirical routines for optimization as is well understood in the art.

Articles of Manufacture

Fusion toxins of the invention can be combined with packaging material and sold as kits for killing tumor cells. Components and methods for producing articles of manufacture such as kits are well known. An article of manufacture may include one or more of the fusion toxins set out in the above sections. In addition, the article of manufacture further may include buffers or other solutions necessary to effect tumor cell death. Instructions describing how the fusion toxins are effective for killing target cells can be included in such kits.

The invention will be further described in the following examples, which do not limit the scope of the invention described in the claims.

EXAMPLES

Example 1 -Materials and Methods

Plasmid construction: The pDTAT.pET21d expression plasmid (FIG. 1) was constructed by ligating a C-terminally truncated fragment of DT and the ATF of uPA, and subcloning the ligation product into pET21d (Promega, Madison, Wis.). To clone the individual cDNA segments with appropriate restriction sites, the cDNA sequence encoding human mature urokinase (Accession No: E01560) and the gene sequence encoding diphtheria toxin (Corynebacteriophage beta (*C. diphtheriae*) gene and flanks; Accession No: K01722) were obtained from GenBank. The uPA ATF was assembled by synthesizing 20 oligonucleotides, each 40 bp in length, which covered both strands over the length of the ATF. Oligonucleotides were designed to place a HindIII restriction site at the 5' end of the assembly, followed by sequences encoding a linker with the amino acid sequence GluAlaSerSerGlyGlyProGlu (SEQ ID NO:1). Oligonucleotides containing a stop codon followed by a XhoI site were positioned at the 3' end of the assembly. The pooled oligonucleotides were used as templates for each other in a single PCR reaction. The amplified product was purified from a 1% agarose gel and subcloned into the pGEM®-T Easy vector (Promega). The fidelity of the product was verified by DNA sequencing (Advanced Genetic Analysis Center, University of Minnesota, St. Paul, Minn.). Mutations were corrected with the QuikChange™ Site-Directed Mutagenesis Kit (Stratagene, La Jolla, Calif.). A gene fragment encoding the first 390 amino acids of diphtheria toxin (389 amino acids plus a methionine start codon) was assembled in an identical fashion and then ligated into the prokaryotic expression vector pET21d at the NcoI and HindIII sites to generate $DT_{390}$.pET21d. The HindIII/XhoI ATF uPA fragment subsequently was subcloned into the $DT_{390}$.pET21d construct to generate DTAT.pET21d (FIG. 1), which encodes the recombinant fusion toxin, DTAT. DTAT therefore consists of $DT_{390}$ and the 135 amino acid ATF of uPA. The DTAT protein product had a predicted MW of 58.1 kDa and an isoelectric point of 6.073.

DTAT expression and purification: The pDTAT.pET21d expression plasmid was transformed into the *E. coli* strain BL21(DE3) (Novagen, Madison, Wis.). Recombinant bacteria were grown on LB plates containing carbenicillin (Sigma, St. Louis, Mo.) at 37° C. for 18 hours. Colonies were scraped and distributed into four 1 L superbroth cultures supplemented with 100 µg/ml carbenicillin, and grown in a 2 L flask at 37° C. When the absorbance ($A_{600}$) reached 0.8, expression of the hybrid gene was induced by the addition of 1 mM isopropyl-β-D-thiogalactopyranoside (IPTG, Gibco/BRL). Twenty-one and a half hours after induction, cells were harvested by centrifugation at 32,000 g for 10 minutes. All four bacterial pellets were resuspended in TE/NaCl (50 mM Tris pH 8.0, 20 mM EDTA, 100 mM NaCl), pooled in a total volume of 200 ml, and transferred into a rosette sonication cup (Sonics and Material Inc., Newton, Conn.). The bacteria were lysed by sonication at 4° C. for 30 minutes. Inclusion bodies were spun down at 14,000 g for 10 minutes and were extracted for 18 hours at 4° C. with 150 ml TE/NaCl containing 5% Triton X-100, 10% glycerin, and 0.3% sodium deoxycholate. The pellet was washed twice with detergent, followed by three washes with TE/NaCl. Partially purified inclusion bodies were solubilized to 10 mg/ml with 0.1 M Tris pH 8.0, 7 M guanidine-HCl, 64 mM DTT, and 2 mM EDTA. Renaturation was initiated by 100-fold dilution of the denatured protein into chilled refolding buffer containing 0.1 M Tris pH 8.0, 0.5 M L-arginine, 0.9 mM GSSG (Calbiochem, San Diego, Calif.) and 2 M EDTA. Samples were incubated at 4° C. for 48 hours. The refolded protein was filtered through a 0.45µ filter and then diluted 10-fold with distilled water. This refolded and diluted protein was purified further passing the samples over a Fast Flow Q-Sepharose column (Sigma) and eluting the protein with a 0 to 1 M NaCl gradient in 20 mM Tris pH 8.0. The DTAT fusion toxin eluted at 0.2 to 0.3 M NaCl, and residual contamination was removed by size-exclusion chromatography on a TSK 250 column (TosoHass, Philadelphia, Pa.), using SDS-PAGE to assess each fraction. The active peak was pooled, concentrated, and dialyzed against PBS.

Cell lines and antibodies: The U118 MG, U87 MG, U373 MG, and T98 G cell lines were derived from human patients diagnosed with glioblastoma multiforme and were provided by Dr. Walter Low, University of Minnesota. The Neuro-2a (murine neuroblastoma), Daudi (human Burkitt's lymphoma), and SKBR3 (human mammary gland adenocarcinoma) lines were obtained from American Type Culture Collection (Manassas, Va.). All cell lines were maintained in RPMI 1640 medium supplemented with 10% heat-inactivated fetal bovine serum (both from Biowhittaker, Walkersville, Md.), and 2 mM L-glutamine, 0.1 mM non-essential amino acids, 1.0 mM sodium pyruvate, and 100 U/ml penicillin/100 µg/ml streptomycin (all from Gibco/BRL). Human umbilical vein endothelial cells (HUVEC) were obtained from Dr. S. Ramakrishnan, University of Minnesota. HUVEC were maintained in Medium 199 (Gibco/BRL) containing 15% heat-inactivated fetal bovine serum, 100 U/ml penicillin/100 µg/ml streptomycin, and Endothelial Cell Growth Medium (Biowhittaker), and were used within seven passages. All cells were maintained at 37° C. in a humidified incubator in 5% $CO_2$/95% air, and passaged two to three times per week.

Polyclonal rabbit anti-human urokinase IgG and a murine IgG2a monoclonal antibody against human urokinase receptor were obtained from American Diagnostica Inc. (Greenwich, Conn.), and were used for blocking experiments. Anti-IL-4 (rat anti-mouse IgG1) was obtained from clone 11B11 (American Type Culture Collection, Manassas, Va.).

Cytotoxicity assay: The in vitro cytotoxicity of DTAT was tested by measuring the incorporation of radiolabeled thymidine into DNA in treated and untreated cells, using a previously described method (Vallera et al. (1997) *Protein Eng.* 10:1071–1076). $10^4$ cells in 100 µl medium were seeded per well on 96-well plates. Following an overnight incubation, cells were cultured in the presence of various concentrations of DTAT for 24, 48, or 72 hours. 1 µCi [methyl-$^3$H]-thymidine (Amersham Pharmacia Biotech UK Limited, Buckinghamshire, England) was added at the beginning of the final 8 hours of incubation. At the end of the incubation, cells were washed and harvested on glass fiber filters, and the incorporation of radioactivity was quantified. Assays were performed in triplicate and repeated 2 to 4 times; data is expressed as the percentage of [$^3$H]-thymidine incorporation in cells incubated without toxin. Statistical significance was assessed by Student's t test. For blocking experiments, cells or toxins were preincubated with antibodies for 30 minutes at 37° C. and the assay was then performed as above.

In vivo studies: Female athymic nu/nu nude mice and C57BL/6 mice 6 to 8 weeks of age were purchased from NIH (Bethesda, Md.), and were maintained in microisolator cages under specific pathogen-free conditions by the Department of Research Animal Resources, University of Minnesota, Minneapolis, Minn. On days -2 and -4, 25 µl anti-asialoGM1 (Wako Chemicals USA, Richmond, Va.) diluted in 175 µl PBS was injected intraperitoneally into each mouse to enhance tumor growth. On day 0, $6 \times 10^6$ U118 MG cells in 0.1 ml culture medium were injected subcutaneously into the right flank of each mouse. Each treatment group consisted of 4 to 5 animals, and mice were examined every 2 to 3 days. Palpable tumors larger than 0.15 $cm^3$ were treated by intratumoral injection beginning on day 28, such that each mouse received an injection of 20 µg DTAT in 50 µl PBS every other day over the course of 9 days (for a total of 5 injections). Control animals received injections of DThIL2 or PBS. Tumor volumes were monitored by caliper measurement of length, width, and height.

Human glioblastoma tumors also were established in the brains of nude mice. Animals were restrained in a rat stereotactic head frame (David Kopf Instruments, Tujunga, Calif.) and intracranially injected with $1 \times 10^5$ U87 MG cells in 3 µl culture medium on study day 0. Initial MRI scans were performed on day 15 post tumor injection, at which time mice were treated with either 5 µg DTAT in 3 µl PBS or PBS alone, injected to the same stereotactic coordinates as the tumor cells. The effects of treatment with DTAT or PBS were determined by MRI scans on day 22 post tumor injection. MRI scans were performed using a Philips 1.5 Tesla MRI scanner (Philips Medical Instruments, Bothell, Wash.).

Histology: Mice were sacrificed and tissues were removed for histopathologic analysis as previously described (Vallera et al., above). Samples were imbedded in OCT (Miles, Elkhart, Ind.), snap frozen in liquid nitrogen, and stored at −80° C. until sectioning. Serial 4 µm sections were thaw mounted onto glass slides, fixed for 5 minutes in acetone, and stained with hematoxylin and eosin for assessment.

Blood Urea Nitrogen (BUN) and alanine transferase (ALT) assays: Both assays were performed as previously described (Vallera et al. (2000) *Cancer Res.* 60:976–984) on a Kodak ETACHEM 950 by the Fairview University Medical Center—University Campus (Minneapolis, Minn.). Mice were sacrificed, serum samples were collected by heart bleeding, and analyses were performed blindly on undiluted samples. The minimum sample volume for each assay was 11 µl. BUN was measured spectrophotometrically at 670 µm, while the oxidation of NADH was used to measure ALT activity at 340 nm.

Example 2 -Effectiveness of DTAT in vitro

Figure 2:
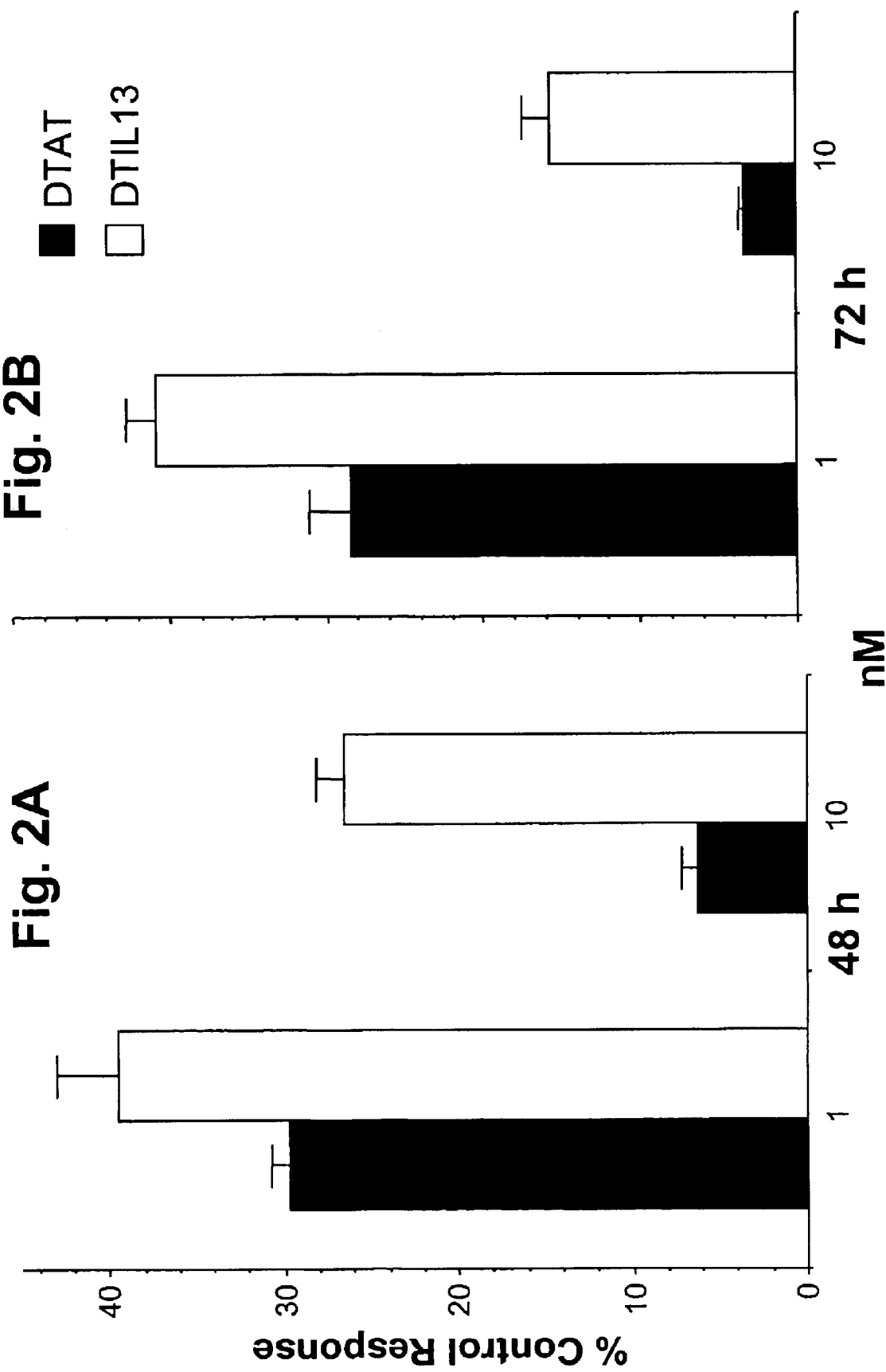

To determine whether an IL13/diphtheria fusion protein would kill human glioblastoma cells, DThIL13 was used in cytotoxicity assays as described in Example 1. DThIL13 completely blocked DNA synthesis in the U373 MG line, with an $IC_{50}$ less than 0.01 nM. In contrast, DNA synthesis in the U87 MG line was inhibited only 45% by 10 nM DThIL13, and the T98 G line was completely unaffected, demonstrating that DThIL13 does not kill all glioblastoma cells. Since uPAR is overexpressed in certain cancers, the effectiveness of DTAT was tested using the U118 MG glioblastoma line. DNA synthesis in these cells was inhibited by approximately 94% after 48 hours of treatment with 10 nM DTAT, while DThIL13 resulted in only a 73% reduction (FIG. 2A). At 72 hours, DTAT had blocked more than 94% of DNA synthesis in the U118 MG cells (FIG. 2B). The difference between DTAT and DThIL13 treatment was statistically significant at both time points ($P<0.05$).

Figure 3:
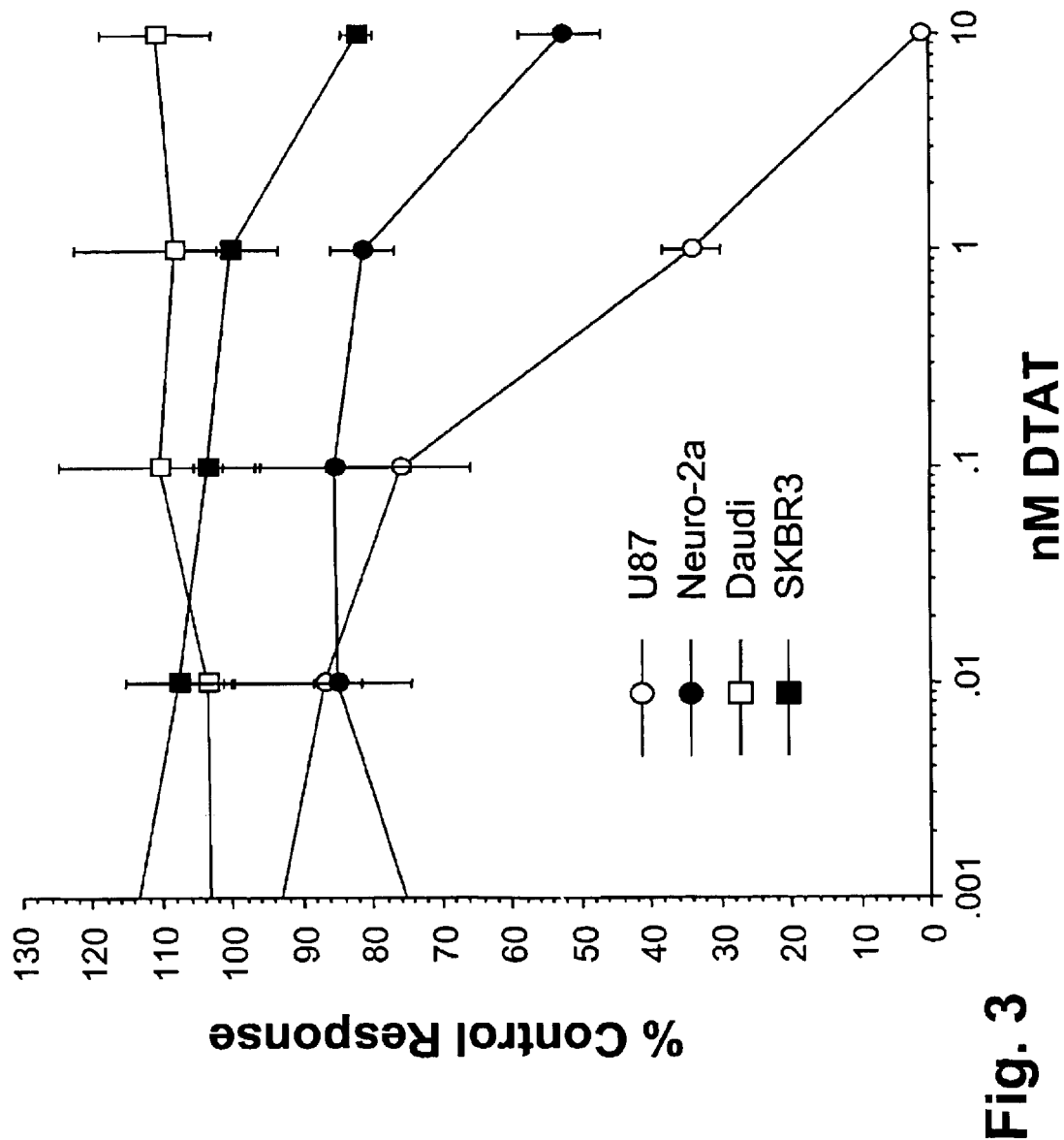
Figure 4:
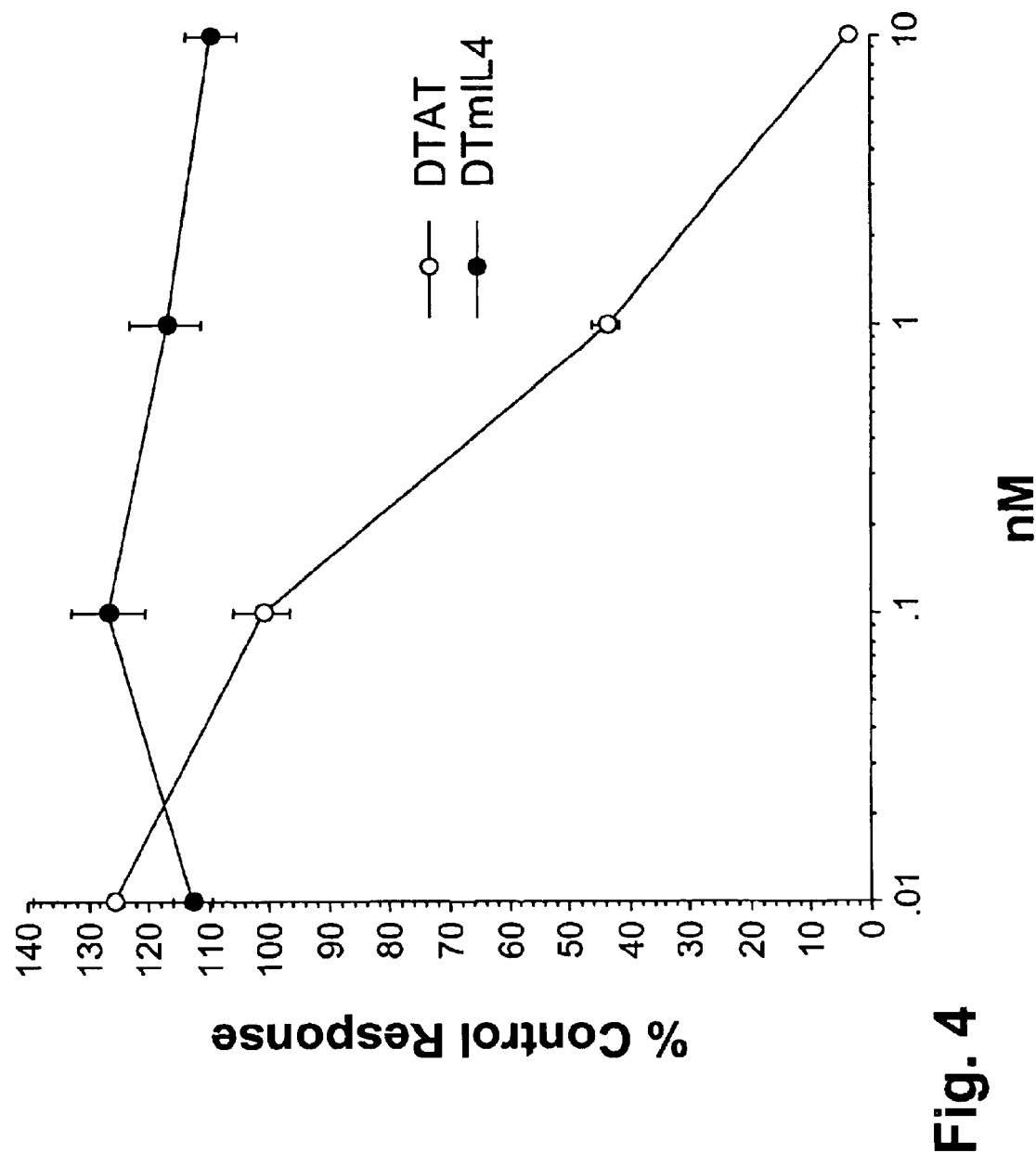

To study the selectivity of DTAT, it was tested in various cell lines that do not express uPAR. DNA synthesis in the U87 MG glioblastoma line was completely inhibited by treatment with 10 nM DTAT for 72 hours ($IC_{50}<1$ nM), while the Daudi lymphoma and SKBR3 mammary gland adenocarcinoma lines were not affected (FIG. 3). DNA synthesis in the Neuro2a murine neuroblastoma line was partially inhibited. To further study selectivity, U118 MG cells were treated with a mouse IL4/diphtheria fusion toxin, used as a negative control since mouse IL4 is species specific and does not bind to human cells. Whereas 10 nM DTAT inhibited DNA synthesis in U118 MG cells after 72 hours, DTmIL4 had no effect (FIG. 4). DTAT is therefore highly selective in its ability to kill receptor-expressing cells.

Figure 5:
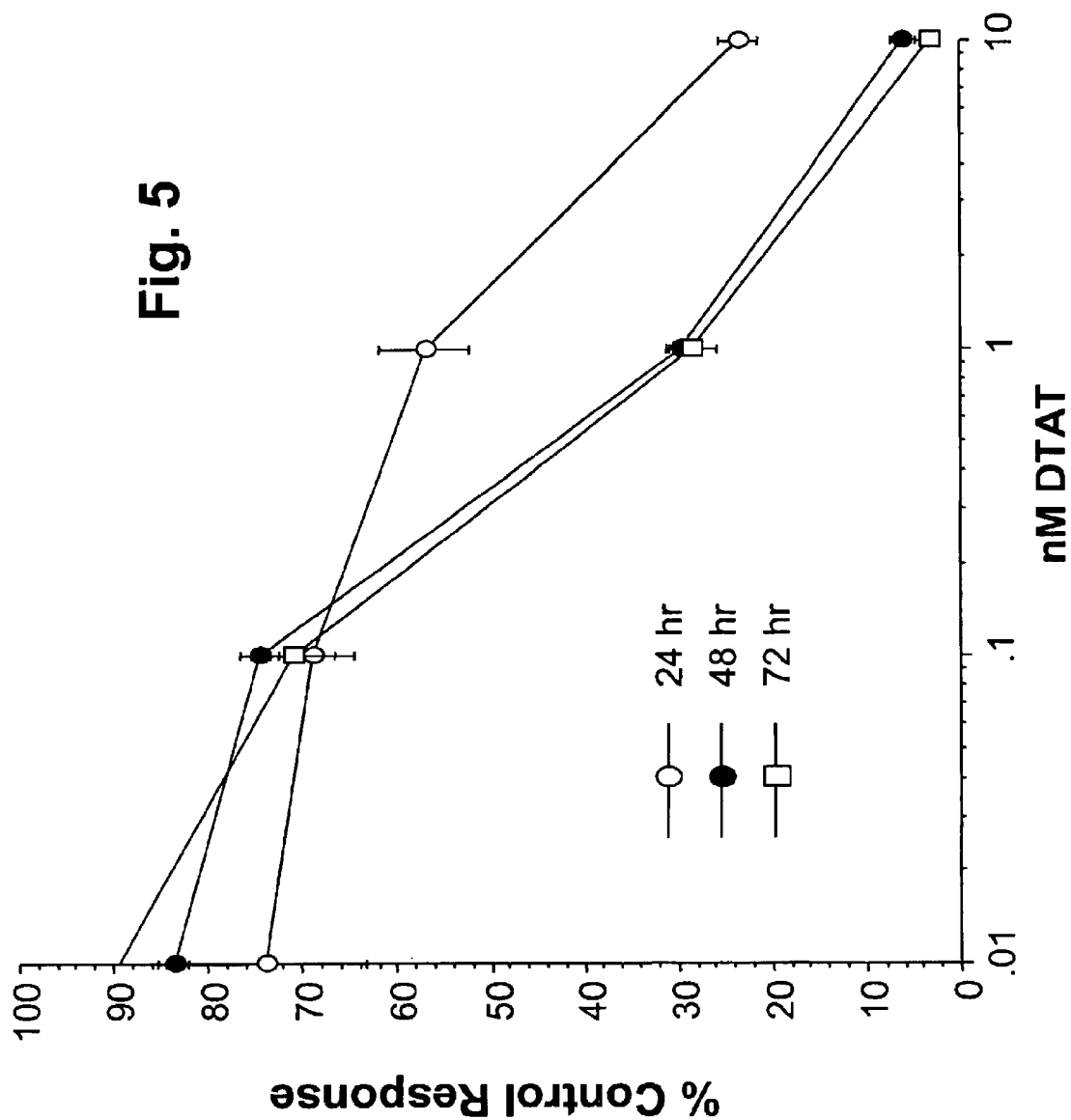

To determine whether exposure of DTAT to its target for longer periods would increase its effectiveness, various concentrations of the fusion toxin were incubated with U118 MG cells for 24, 48, and 72 hours. These dose response/time course studies revealed that maximal toxicity was observed after 48 hours, and exposure to DTAT for 72 hours did not enhance cytotoxicity (FIG. 5).

Figure 6:
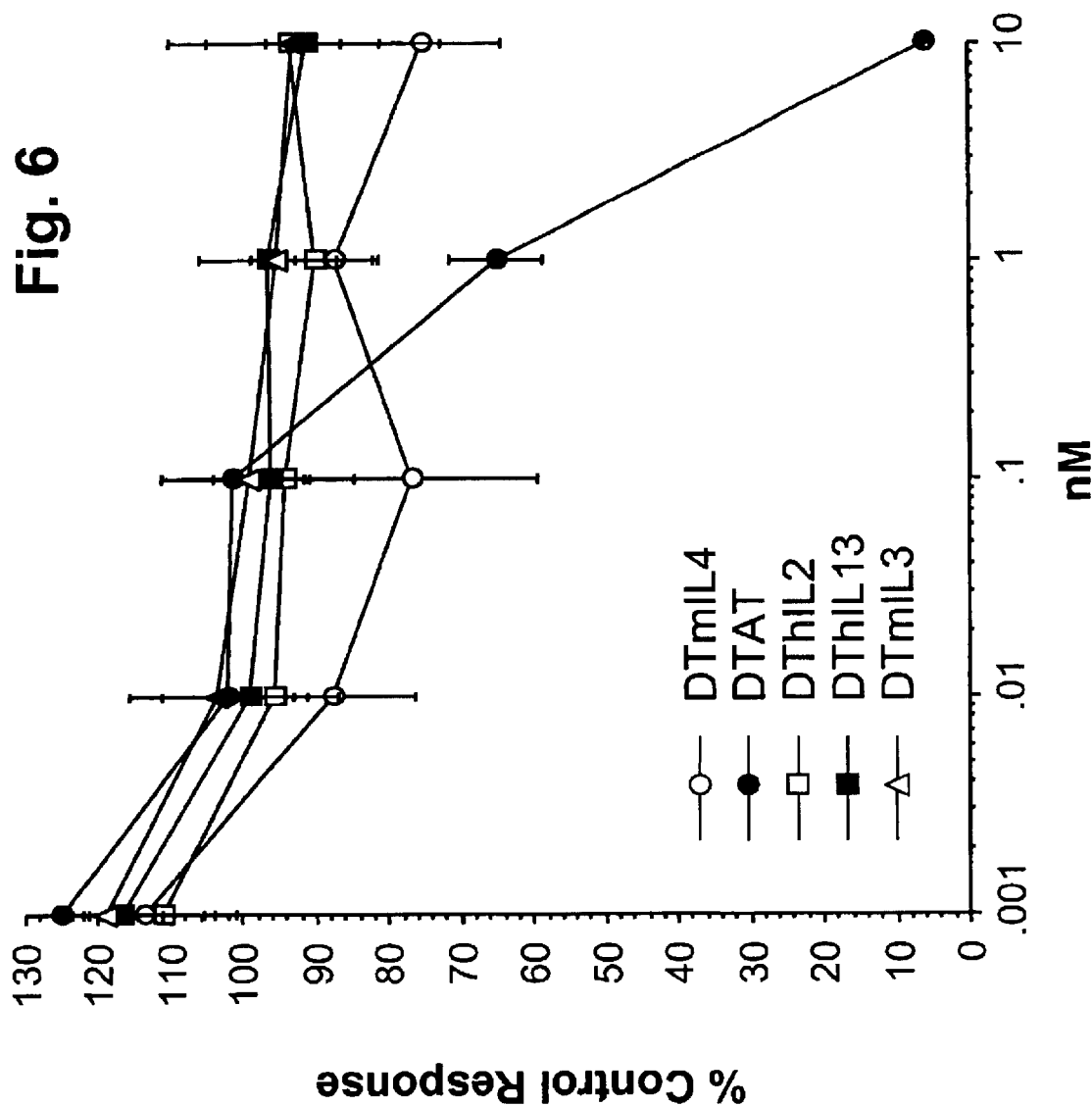

As mentioned above, the ability of DTAT to bind to a tumor and its microvasculature could provide a therapeutic advantage since tumor growth is dependent on a thriving vasculature. To assess the effectiveness of DTAT on vascular cells, the fusion toxin was incubated with HUVEC. DTAT was able to inhibit the proliferation of HUVEC in a dose dependent manner, with an $IC_{50}$ of about 1 nM after 72 hours of treatment (FIG. 6). In contrast, a number of control fusion toxins that bind to receptors not found on HUVEC (including mIL4R, hIL2R, hIL13R, and mIL13R) were much less cytotoxic.

Figure 7:
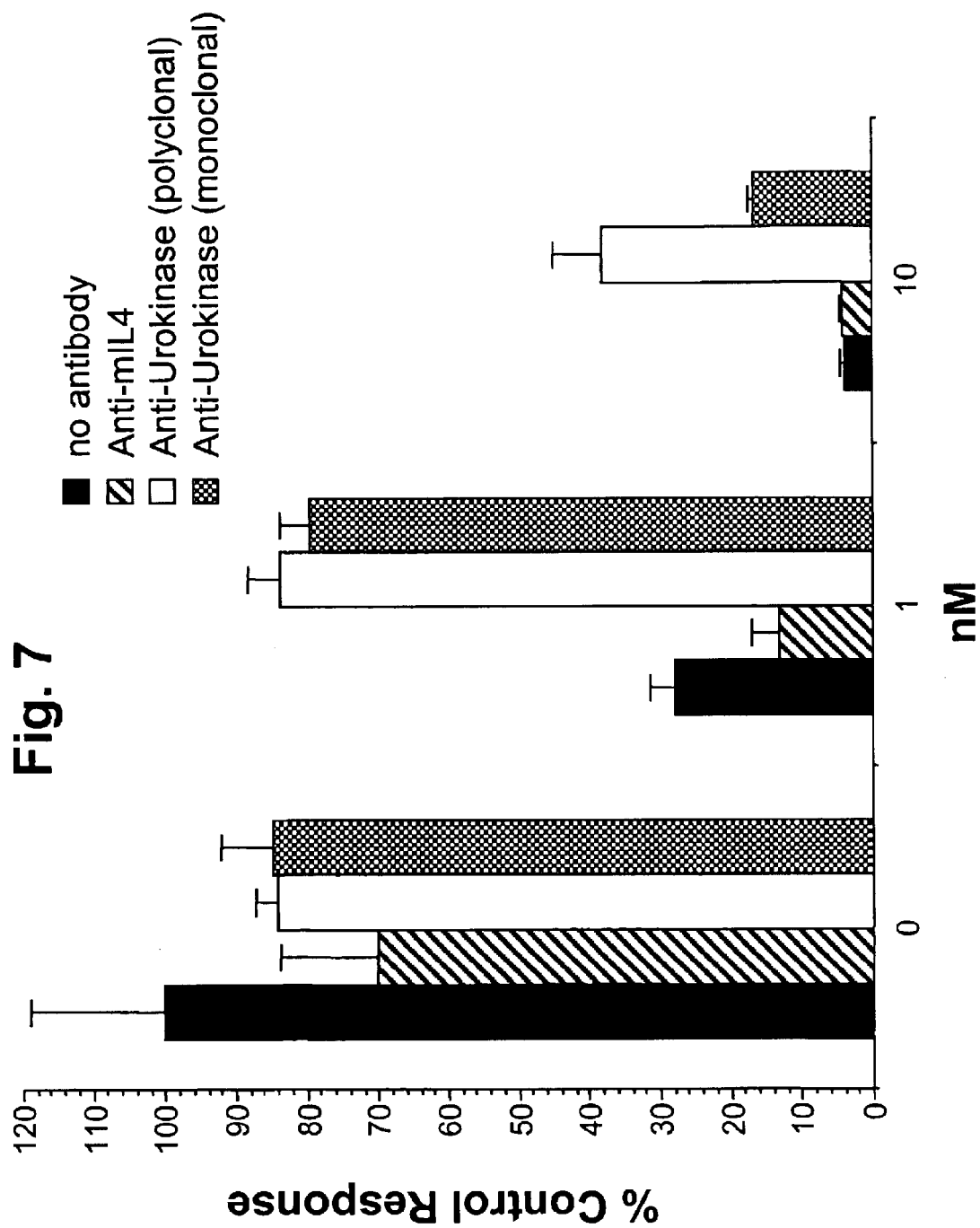

To ascertain whether the activity of DTAT was mediated by the ATF, DTAT was preincubated with a monoclonal or polyclonal anti-urokinase antibody before administration to HUVEC, as described in Example 1. Such treatment completely blocked the cytotoxic effect of 1 nM DTAT and reduced the effectiveness of 10 nM DTAT, whereas a control anti-mouse IL4 antibody had no effect (FIG. 7). Together, these results demonstrate that DTAT selectively kills endothelial cells in vitro through its ability to bind uPAR.

Example 3 - Effectiveness of DTAT in vivo

Figure 8:
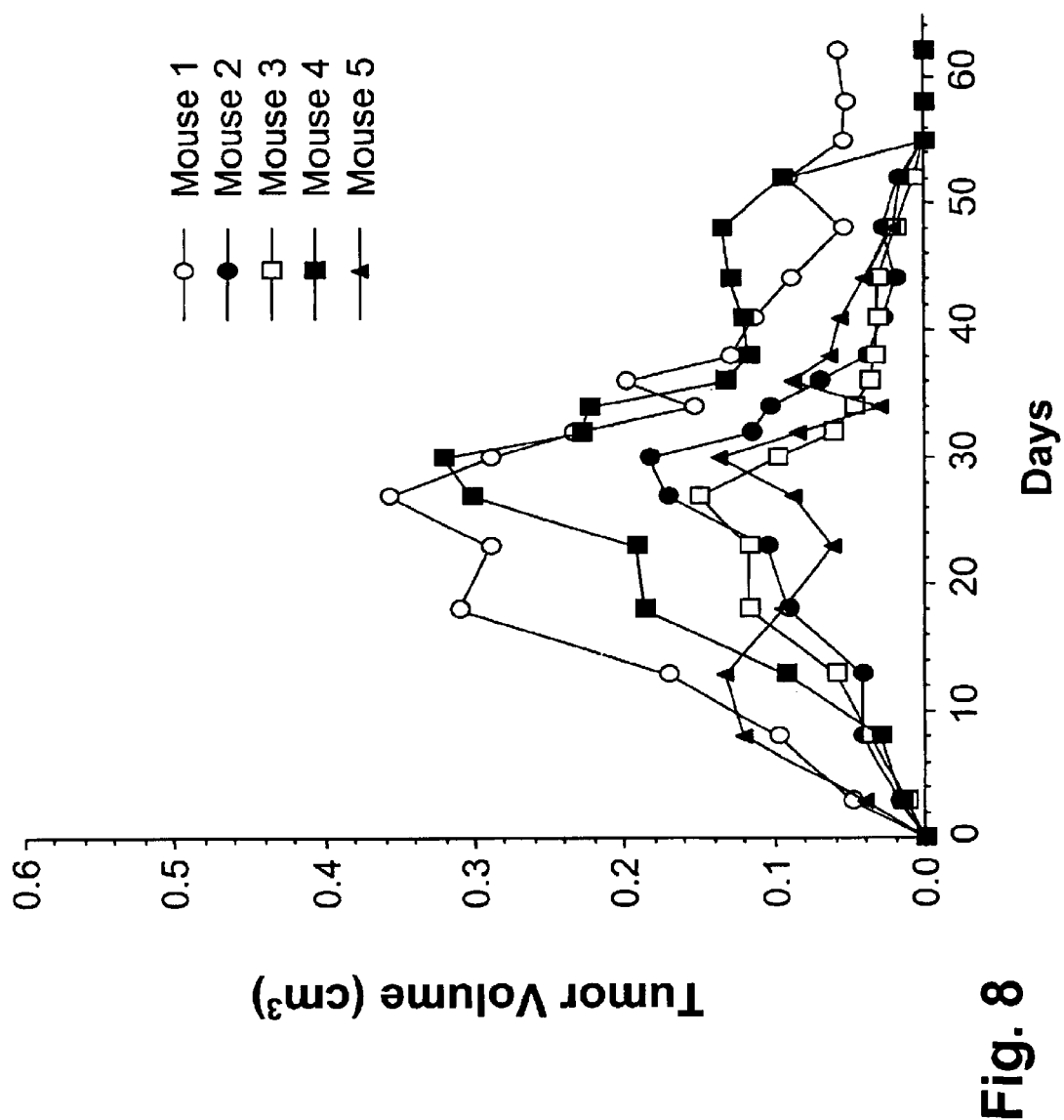
Figure 9:
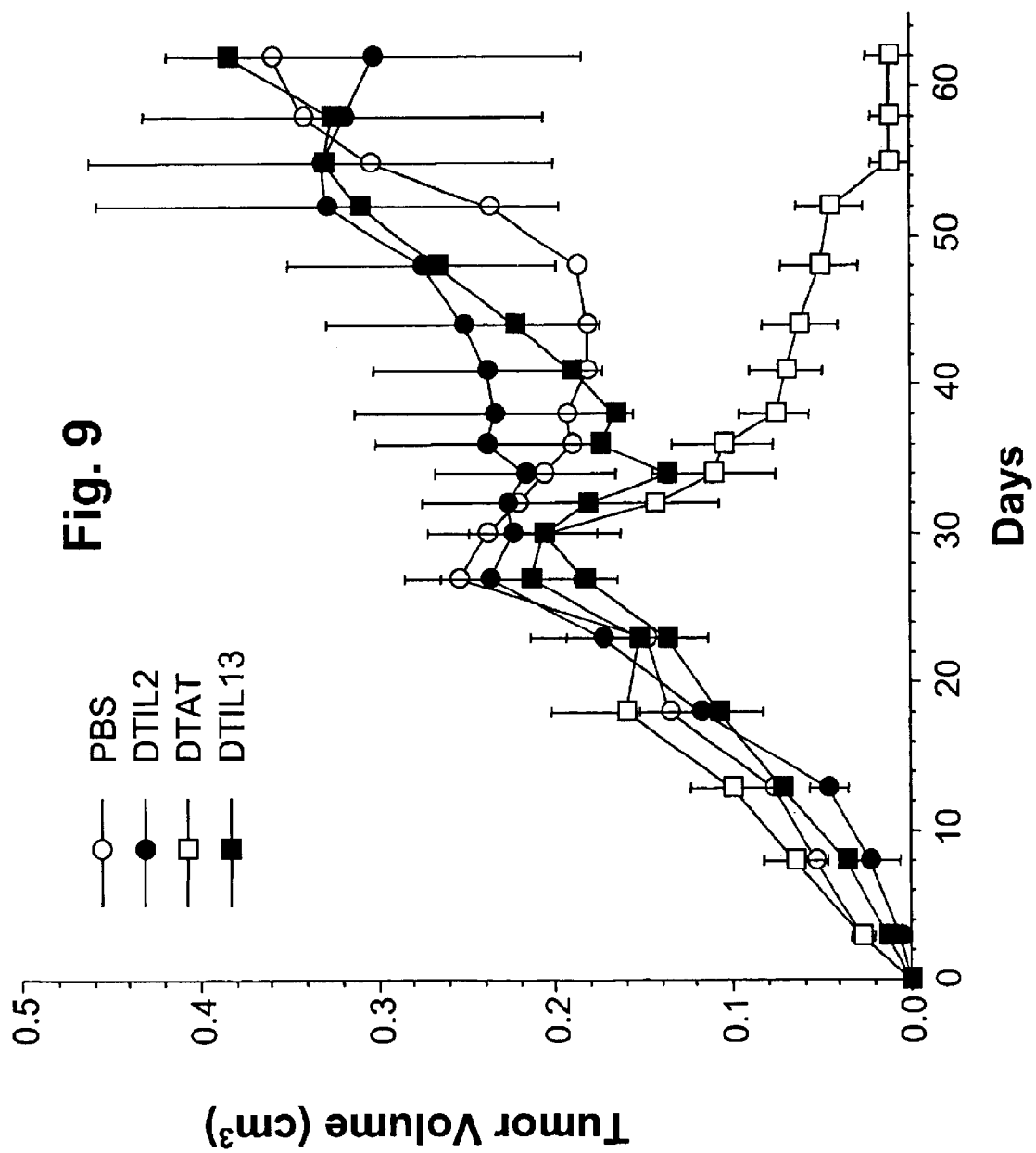

To determine the effectiveness of DTAT in vivo, a nude mouse model of human glioblastoma was established. U118 MG cells were inoculated into the flanks of nude mice as described in Example 1. After 28 days, mice with established tumors were given a course of DTAT. In a test group of five mice, all tumors regressed following a 5 dose course of 20 μg DTAT injected directly into each tumor every other day. Tumors continued to shrink during the days following treatment such that by study day 62 all but one tumor had completely regressed (FIG. 8). In contrast, tumors in groups of mice treated with DThIL2, DThIL13, or PBS did not regress over the study period, and in fact continued to increase in size (FIG. 9). There was a significant difference in the tumor growth curves on day 48 when the DTAT group was compared to the control groups (P<0.05). These in vivo observations are correlated with the results of the in vitro toxicity studies, and support the hypothesis that DTAT might be a useful treatment for tumors not responsive to DTIL13.

To examine the effectiveness of DTAT for treating brain tumors, a second model of human glioblastoma was established in nude mice. U87 MG cells were injected intracranially as described in Example 1. MRI scans were performed on day 15 post injection to verify the presence of tumors, which were visualized in coronal MRI frames taken in 1 mm slices from each mouse. Two mice then were treated with 5 μg DTAT, administered to the same stereotactic coordinates as the tumor cells, while the third mouse was treated with PBS. MRI scans were repeated on day 22 post tumor injection. The tumor in the control mouse continued to grow after PBS treatment. The mice treated with DTAT, however, displayed significant tumor regression. The tumor size was reduced approximately 95% in one DTAT-treated mouse, while no evidence of tumor was found in the other DTAT-treated mouse.

To assess potentially toxic effects of DTAT on areas outside tumors, control animals without tumors were subcutaneously injected with 20 μg DTAT every other day for a total of 5 doses and tissues sections and blood samples were obtained the day after the final injection. Frozen sections were stained and serum analyses were performed as described in Example 1. Kidney tissue appeared unaffected by DTAT treatment, with the exception of some minor neutrophil infiltration. In addition, there was no significant fluctuation in BUN levels following DTAT treatment (FIG. 10A), indicating that DTAT does not interfere with renal activity. These studies were particularly important because similar doses of immunotoxins in other studies had induced glomerular destruction, rupture of renal tubules, and proximal tubular vacuolization (Vallera et al. (1997), above). As a control, a separate group of mice was treated with DTantiCD3sFv, a fusion toxin previously shown to mediate renal damage. DTantiCD3sFv caused a significant elevation in BUN activity (FIG. 10A), and histology studies confirmed glomerular damage and tubular rhexis.

Histologic examination revealed that liver tissue was relatively unaffected by DTAT treatment, other than in a few areas that exhibited small amounts of infiltration. DTAT also had no effects on heart or spleen. Functional analysis revealed a significant, albeit non-life-threatening elevation in ALT levels (FIG. 10B). Although this elevation was not indicative of liver failure, and histology indicated that the liver was intact, it appeared that DTAT did affect the liver at this dose. However, these studies were done in normal, non-tumorigenic mice. It is possible that a tumor and its extensive vascular network could act as an "antigenic sink" to absorb injected DTAT and limit the amount that would leave the tumor. Furthermore, the absence of this "antigenic sink" in the tumor-free control mice injected with DTAT may have resulted in greater toxic stress on the liver, thus explaining the elevated ALT levels. Preliminary experiments indicating that mice with large (>6 $cm^3$) subcutaneous tumors were able to tolerate a 100 μg/dose course of DTAT provide support for this possibility.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for killing a tumor cell, comprising contacting said tumor cell with a fusion toxin comprising the toxin domain of diphtheria toxin and a urokinase-type plasminogen activator domain, wherein said contacting occurs in vivo, and wherein there exists an amount of said fusion toxin that:

(a) does not result in life-threatening hepatic toxicity when said fusion toxin is administered subcutaneously; and (b) results in a decrease in the size of a tumor when said fusion toxin is administered into said tumor.

2. The method of claim 1, wherein said tumor cell is a brain tumor cell.

3. The method of claim 2, wherein said brain tumor is selected from the group consisting of glioblastoma, meningioma, astrocytoma, medulloblastoma, ependymoma, and oligodendroglioma.

4. The method of claim 2, wherein said brain tumor is a glioblastoma.

5. The method of claim 1, wherein said tumor cell expresses the urokinase-type plasminogen activator receptor.

6. The method of claim 1, wherein said fusion toxin comprises the translocation enhancer region of diphtheria toxin.

7. The method of claim 1, wherein said fusion toxin comprises the amino terminal 390 amino acids of diphtheria toxin.

8. The method of claim 1, wherein said urokinase-type plasminogen activator domain is capable of binding to urokinase-type plasminogen activator receptor.

9. The method of claim 8, wherein said urokinase-type plasminogen activator domain comprises the amino terminal fragment of urokinase-type plasminogen activator.

10. The method of claim 1, wherein said fusion toxin comprises the toxin domain of diphtheria toxin, the translocation enhancing region of diphtheria toxin, and the amino-terminal fragment of urokinase-type plasminogen activator.

11. A method for killing a glioblastoma tumor cell, comprising contacting said glioblastoma tumor cell with a fusion toxin comprising a urokinase-type plasminogen activator domain, wherein said contacting occurs in vivo, and wherein there exists an amount of said fusion toxin that:

(a) does not result in life-threatening hepatic toxicity when said fusion toxin is administered subcutaneously; and (b) results in a decrease in the size of a tumor when said fusion toxin is administered into said tumor.

12. The method of claim 11, wherein said fusion toxin comprises a toxin domain of a toxin selected from the group consisting of diphtheria toxin, ricin, Pseudomonas exotoxin, colicin, anthrax toxin, tetanus toxin, botulinum neurotoxin, saporin, abrin, bryodin, pokeweed anti-viral protein, viscumin, and gelonin.

13. The method of claim 11, wherein said fusion toxin comprises the toxin domain of diphtheria toxin.

14. The method of claim 11, wherein said fusion toxin comprises an internalization domain of a toxin selected from the group consisting of diphtheria toxin, colicin, delta-Endotoxin, anthrax toxin, tetanus toxin, botulinum toxin, and Pseudomonas exotoxin.

15. The method of claim 11, wherein said fusion toxin comprises the translocation enhancing region of diphtheria toxin.

16. The method of claim 11, wherein said urokinase-type plasminogen activator domain is capable of binding to urokinase-type plasminogen activator receptor.

17. The method of claim 16, wherein said urokinase-type plasminogen activator domain comprises the amino-terminal fragment of urokinase-type plasminogen activator.

18. The method of claim 11, wherein said glioblastoma tumor cell expresses the urokinase-type plasminogen activator receptor.

19. The method of claim 11, wherein said fusion toxin comprises the toxin domain of diphtheria toxin, the translocation enhancing region of diphtheria toxin, and the amino-terminal fragment of the urokinase-type plasminogen activator.

20. A pharmaceutical composition, comprising a fusion toxin, wherein said fusion toxin comprises the toxin domain of diphtheria toxin and a urokinase-type plasminogen activator domain, and wherein there exists an amount of said fusion toxin that:

(a) does not result in life-threatening hepatic toxicity when said fusion toxin is administered subcutaneously; and (b) results in a decrease in the size of a tumor when said fusion toxin is administered into said tumor.

21. An article of manufacture, comprising packaging material and the pharmaceutical composition of claim 20.

22. The pharmaceutical composition of claim 20, wherein said fusion toxin further comprises the translocation enhancing region of diphtheria toxin.

23. The pharmaceutical composition of claim 20, wherein said urokinase-type plasminogen activator domain comprises the amino-terminal fragment of urokinase-type plasminogen activator.

24. The pharmaceutical composition of claim 20, wherein said toxin comprises the toxin domain of diphtheria toxin, the translocation enhancing region of diphtheria toxin, and the amino-terminal fragment of urokinase-type plasminogen activator.

* * * * *